(12) United States Patent
Cully (10) Patent No.: US 9,545,323 B2
(45) Date of Patent: Jan. 17, 2017

(54) FENESTRATION DEVICES, SYSTEMS, AND METHODS (75) Inventor: Edward H. Cully, Flagstaff, AZ (US)

(73) Assignee: W. L. GORE & ASSOCIATES, INC., Newark, DE (US)

( * ) Notice: Subject to any disclaimer, the term of this patent is extended or adjusted under 35 U.S.C. 154(b) by 475 days.

(21) Appl. No.: 13/295,817

(22) Filed: Nov. 14, 2011

(65) Prior Publication Data

US 2012/0136385 A1   May 31, 2012

Related U.S. Application Data (60) Provisional application No. 61/414,155, filed on Nov. 16, 2010.

(51) Int. Cl.
A61F 2/958 (2013.01)
A61F 2/07 (2013.01)
A61B 1/00 (2006.01)
A61B 18/14 (2006.01)
A61F 2/06 (2013.01)
A61M 25/10 (2013.01)
A61F 2/89 (2013.01)

(52) U.S. Cl.
CPC .............. *A61F 2/958* (2013.01); *A61F 2/07* (2013.01); *A61B 1/00082* (2013.01); *A61B 1/00085* (2013.01); *A61B 1/00154* (2013.01); *A61B 18/1492* (2013.01); *A61F 2/89* (2013.01); *A61F 2002/061* (2013.01); *A61F 2250/0007* (2013.01); *A61M 2025/1045* (2013.01)

(58) Field of Classification Search
CPC . A61F 2/013; A61B 17/0469; A61B 17/0682; A61B 17/00082; A61B 17/00085; A61M 2025/1045

USPC ........ 606/139, 142–148, 153, 191–194, 200; 623/1.11, 2.11
See application file for complete search history.

(56) References Cited

U.S. PATENT DOCUMENTS 3,799,172 A    3/1974  Szpur
5,456,667 A *  10/1995 Ham et al. .................... 604/107
5,617,878 A    4/1997  Taheri
(Continued)

FOREIGN PATENT DOCUMENTS

WO    94/21169    9/1994
WO    99/42044    8/1999
(Continued)

OTHER PUBLICATIONS

Manning, BJ, Ivancev, K. Techniques for Supra-aortic trunk Preservation in Thoracic Endovascular Aneurysm Repair. Acta Chir Belg, 2010, 110; 112-115.

(Continued)

*Primary Examiner* — Alexander Orkin (57) ABSTRACT

The present disclosure provides methods and apparatuses for guiding an endovascular tool, such as a puncturing tool or an angioscope, in a radial direction, such as toward or through the sidewall of a vessel, stent, or stent graft, using elongate members and specialized catheters. The present disclosure provides methods and apparatuses for locating branch vessels from within a grafted main vessel while maintaining continuous blood flow to the branch vessel. Another aspect of the present disclosure involves a reverse cannulation system, particularly useful for stenting the abdominal aorta proximate the renal arteries and stenting the renal artery.

21 Claims, 11 Drawing Sheets (56) References Cited

U.S. PATENT DOCUMENTS

| | | | |
|---|---|---|---|
| 5,795,322 A | 8/1998 | Boudewijn | |
| 5,810,874 A | 9/1998 | Lefebvre | |
| 5,916,194 A | 6/1999 | Jacobsen et al. | |
| 5,928,260 A * | 7/1999 | Chin et al. | 606/200 |
| 6,099,497 A * | 8/2000 | Adams | A61F 2/856 |
| | | | 604/101.01 |
| 6,461,522 B1 * | 10/2002 | Pak et al. | 210/759 |
| 6,579,261 B1 | 6/2003 | Kawamura | |
| 6,592,593 B1 | 7/2003 | Parodi et al. | |
| 6,652,567 B1 | 11/2003 | Deaton | |
| 6,699,260 B2 | 3/2004 | Dubrul et al. | |
| 6,814,752 B1 | 11/2004 | Chuter | |
| 7,192,439 B2 | 3/2007 | Khairkhahan et al. | |
| 7,291,146 B2 | 11/2007 | Steinke et al. | |
| 7,547,304 B2 | 6/2009 | Johnson | |
| 8,403,927 B1 | 3/2013 | Shingleton | |
| 8,409,224 B2 * | 4/2013 | Shriver | A61B 17/11 |
| | | | 606/144 |
| 2002/0026217 A1 | 2/2002 | Baker et al. | |
| 2003/0023248 A1* | 1/2003 | Parodi | 606/139 |
| 2003/0040712 A1* | 2/2003 | Ray | A61M 25/0084 |
| | | | 604/173 |
| 2003/0176767 A1* | 9/2003 | Long | A61B 1/0014 |
| | | | 600/106 |
| 2004/0106972 A1 | 6/2004 | Deaton | |
| 2005/0209506 A1 | 9/2005 | Butler et al. | |
| 2005/0209677 A1* | 9/2005 | Shaked | A61F 2/856 |
| | | | 623/1.11 |
| 2006/0074475 A1* | 4/2006 | Gumm | 623/1.11 |
| 2007/0043389 A1* | 2/2007 | Shindelman | A61M 25/1011 |
| | | | 606/194 |
| 2007/0208256 A1 | 9/2007 | Marilla | |
| 2007/0225750 A1* | 9/2007 | Ren et al. | 606/200 |
| 2007/0244547 A1 | 10/2007 | Greenan | |
| 2008/0097481 A1* | 4/2008 | Schorr et al. | 606/144 |
| 2008/0140180 A1 | 6/2008 | Dolan et al. | |
| 2008/0147173 A1 | 6/2008 | Mciff et al. | |
| 2008/0234717 A1 | 9/2008 | Bruszewski | |
| 2008/0306586 A1* | 12/2008 | Cartledge | A61B 17/00234 |
| | | | 623/2.11 |
| 2009/0125097 A1 | 5/2009 | Bruszewski et al. | |
| 2009/0157164 A1 | 6/2009 | McKinsey et al. | |
| 2009/0228020 A1 | 9/2009 | Wallace et al. | |
| 2009/0234348 A1 | 9/2009 | Bruszewski et al. | |
| 2009/0259290 A1 | 10/2009 | Bruszewski et al. | |
| 2009/0264821 A1 | 10/2009 | Mafi et al. | |
| 2009/0264976 A1 | 10/2009 | Nagasrinivasa | |
| 2009/0264988 A1 | 10/2009 | Mafi et al. | |
| 2009/0264990 A1 | 10/2009 | Bruszewski | |
| 2009/0264991 A1 | 10/2009 | Paul, Jr. et al. | |

FOREIGN PATENT DOCUMENTS

| | | |
|---|---|---|
| WO | 99/42047 | 8/1999 |
| WO | 2007/082343 | 7/2007 |
| WO | 2008/124222 | 10/2008 |
| WO | 2009/014865 | 1/2009 |
| WO | 2010/127040 | 11/2010 |

OTHER PUBLICATIONS

McWilliams, RG, et al. Retrograde Fenestration of Endoluminal Grafts From Target Vessels: Feasibility, Technique, and Potential Usage. J Endovasc Ther, 2003;10:946-952.

Sonesson, B, et al. Endovascular total aortic arch replacement by in situ stent graft fenestration technique. J Vasc Surg 2009;49:1589-91.

* cited by examiner

FENESTRATION DEVICES, SYSTEMS, AND METHODS

CROSS REFERENCE TO RELATED APPLICATIONS

This application claims the benefit of U.S. Provisional Patent Application No. 61/414,155 filed on Nov. 16, 2010, the disclosure of which is hereby incorporated by reference in its entirety.

BACKGROUND

Field

The present disclosure relates to the field of endoluminal products, and more particularly, to the field of fenestration devices, systems, and methods.

Discussion of the Related Art

Endovascular surgery is a minimally invasive method of treating vascular diseases from inside the blood vessel. Benefits of minimally invasive procedures include shorter hospital stays, quicker recoveries, and lower risk of complications. Difficulties with endovascular procedures include traversing irregularly shaped, highly tortuous, heavily branched, and very narrow vessels to gain access to the treatment site, and once access is gained, difficulties further include fine-tuning the rotational and lateral position of the tool. Another difficulty relates to maintaining continued blood flow through the vessels during the course of treatment.

When a stent graft is deployed, branch vessels in the proximity of the stent graft can become sealed off from the flow of blood. In order to maintain blood flow, the graft must be fenestrated at the branch vessel junction. This can be problematic because stent graft materials are typically very strong and durable in order to survive conditions within a mobile host vessel for many years, and puncturing this durable material endovascularly adds to the difficulty of the task. Procedures within the aorta present even more challenges, as compared to other vascular treatment sites, because the size and shape of the aorta and the dynamics of blood flow.

Safe preservation of blood flow to the supra-aortic branches during the procedure and subsequently is desirable. In situ fenestration of aortic devices has the potential to allow for continued perfusion of supra-aortic branches, without the need for extra-anatomic bypass, and without the need for custom-made devices. The angle formed by the branch vessel relative to the main vessel is an obstacle to success with this technique Therefore, a need exists to develop better devices, systems, and methods for endovascular treatment of vessels that permit more accurate positioning and continued blood flow, especially with respect to in situ fenestration of aortic devices. In addition, a need exists for incorporating multiple tools within a single device capable of accurate positioning and continued blood flow that canalize the selected sites.

SUMMARY

The present disclosure is generally directed toward devices, systems and methods for guiding an endovascular tool, such as a puncturing tool or an angioscope, in a radial or askew direction, such as toward or through the sidewall of a vessel or a stent device, as that term is defined herein, using cooperative elongate members. The present disclosure is generally directed toward devices, systems and methods for locating branch vessels from within a grafted main vessel and directing endovascular tools to the branch-main vessel junction. Illustrative embodiments may be useful to pierce grafts or stent-grafts to create fenestrations. Illustrative embodiments may be useful to treat aneurysms, dissections, and other pathologies located in the aortic arch. Illustrative embodiments may be useful in connection with the treatment of coronary artery disease, peripheral vascular diseases, portal hypertension, carotid artery disease, renal vascular hypertension, amongst other conditions affecting anatomical conduits. Illustrative embodiments may also be useful to deliver drugs or other implantable devices to specific treatment sites.

BRIEF DESCRIPTION OF THE DRAWINGS

The accompanying drawings provide a further understanding of the present disclosure and are incorporated in and constitute a part of this specification, illustrate embodiments of the disclosure, and together with the description serve to explain the principles of the disclosure.

DETAILED DESCRIPTION OF THE ILLUSTRATED EMBODIMENTS

Persons skilled in the art will readily appreciate that various aspects of the present disclosure may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

The terms "proximal" and "distal," when used herein in relation to a device or device component refer to directions closer to and farther away from the operator of the device. Since the present disclosure is not limited to peripheral or central approaches, the device should not be narrowly construed when using the terms proximal or distal since device features may be slightly altered relative to the anatomical features and the device position relative thereto.

The present disclosure is directed toward devices, systems and methods for guiding an endovascular tool, such as a puncturing tool or an angioscope, in a radial or askew direction, such as toward or through the sidewall of a vessel or a stent device, as that term is defined herein using elongate members and specialized catheters. The present disclosure is directed toward devices, systems and methods for locating branch vessels from within a grafted main vessel and directing endovascular tools to the branch-main vessel junction. Illustrative embodiments may be useful to pierce grafts or stent-grafts to create fenestrations. Illustrative embodiments may be useful to treat aneurysms, dissections, and other pathologies located in the aortic arch. Illustrative embodiments may be useful in connection with the treatment of coronary artery disease, peripheral vascular diseases, portal hypertension, carotid artery disease, renal vascular hypertension, amongst other conditions affecting anatomical conduits. Illustrative embodiments may also be useful to deliver drugs and other implantable devices to specific treatment sites.

As used herein, a "vessel" may be an artery, vein, capillary or the like, or any other anatomical passageway such as stomach or intestine, conduit or lumen existing in a healthy subject. As used herein, "connected" means to join, couple, attach two or more elements whether directly or indirectly, whether permanently or temporarily. As used herein, a "stent device" may refer to a graft, a stent, stent graft, or any other device that may require a fenestration.

In accordance with an embodiment, a guide device is deployable through a vessel to a treatment site. The guide device deploys an endovascular tool to the treatment site and directs or channels the tool in a direction generally normal or off axis to the longitudinal axis of a stent device. In a further embodiment, the guide device may be detectable within the body with the use of ex vivo detectors, thereby facilitating the generally accurate positioning of the guide device.

A guide device may comprise an expandable member configured to expand radially and a guide tube operatively coupled to the expandable member to channel or guide an endovascular tool in an askew, generally radial, or generally orthogonal direction. Askew, as used herein, describes a direction that is generally at an angle from the path of delivery. In an embodiment, the expandable member bends or extends outwardly and thus expands in response to a compression force that may be applied via the longitudinal displacement of an elongate member relative to another elongate member. In other embodiments, an inflatable member may facilitate the expansion of the expandable member. The distal end of the guide tube or other portions may comprise radiopaque material to facilitate generally accurate positioning within the body.

Method of use may comprise deploying through a vessel the guide device to a treatment site, and may further comprise outwardly extending or expanding an expandable member and channeling a subsequent tool (e.g., for puncture, cannulation, etc.) to the selected target. The guide device may be positioned with the use of a detector. An endovascular tool may be deployed through the guide device to the selected treatment site.

Other aspects of the present disclosure involve endovascular targets that are configured to anchor into a branch vessel and facilitate fenestration of an aortic graft, stent, or stent graft while maintaining continuous aortic downstream perfusion throughout the stent deployment and fenestration.

Another aspect involves a reverse cannulation system, particularly useful for stenting the abdominal aorta proximate the renal arteries and stenting the renal artery. An embodiment of the system comprises a puncturing tool entering and piercing a stent graft from the renal artery side, a snare device entering from the abdominal aorta side. The snare device captures the puncture tool and pulls the tool with its accompanying guidewire through to the abdominal aorta access point. A stent device is deployed along this guide wire to stent the renal artery.

Persons skilled in the art will appreciate that the embodiments described herein may be useful in, amongst other things, endovascular treatments to remotely turn or angle endovascular tools with some degree of precision, to make in-situ fenestrations at an angle, to pierce sidewalls of strong, durable graft material in-situ, to maintain the perfusion of branch vessels, and to cross or create one or more ducts through a wide variety of anatomical features.

In accordance with an embodiment, and with reference to FIGS. 1A, 1B, 2A and 2B, a guide device 200 may be structurally or materially configured to deploy an endovascular tool or implant to the treatment site and channel the tool in a direction 251 generally radial, generally orthogonal, or otherwise off axis from its path of delivery 250. An "endovascular tool" comprises any tool capable of use in endovascular procedures, such as a puncturing tool as described herein, piercing catheter, re-entry device, dual-lumen re-entry device, an angioscope, an elongate member, a guide device as described herein, an endovascular target as described herein, a stent, a stent graft, a drug delivery tool, amongst other endovascular tools, and combinations thereof. Exemplary "piercing catheters," "re-entry devices," "dual-lumen re-entry devices," and combinations thereof are more fully described in U.S. patent application Ser. No. 13/273,111 to Cully et al., entitled "System and Method of Percutaneous Occlusion Crossing," hereby incorporated by reference in its entirety.

In accordance with an embodiment, guide device 200 comprises an expandable member 210 and a guide tube 240 operatively coupled to expandable member 210 and having a distal tip 241, which is movable between a first position generally parallel with expandable member 210 in a collapsed position and a second position askew to the first position.

Figures 1A, 1B:
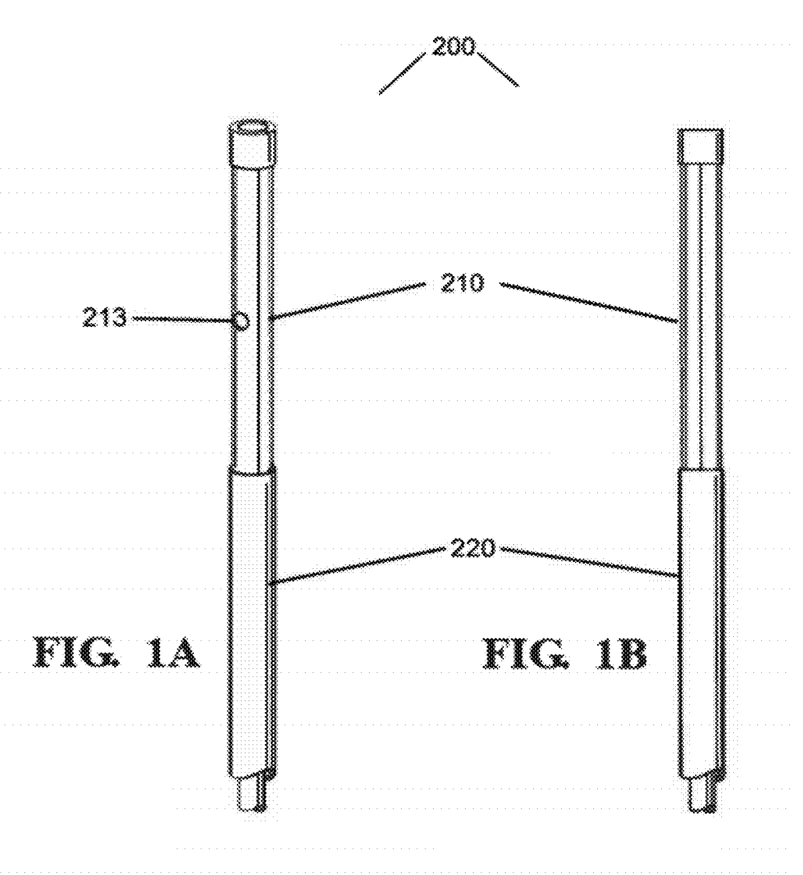
FIG. 1A illustrates a perspective view of an embodiment in a collapsed position.
FIG. 1B illustrates a side view of an embodiment in a collapsed position.
Figures 2A, 2B:
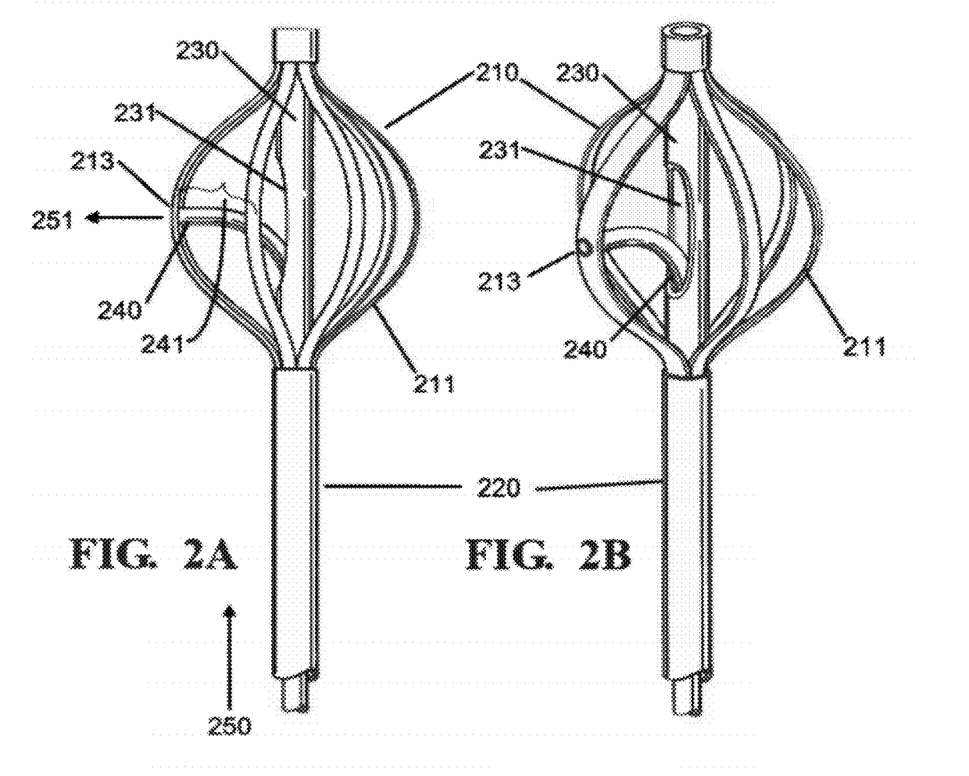
FIG. 2A illustrates a side view of an embodiment in an expanded position.
FIG. 2B illustrates a perspective view of an embodiment in an expanded position.

Expandable member 210 comprises a radially expandable or outwardly extending structure that is movable between a collapsed position and an expanded position. Expandable member 210 may be structurally or materially configured to expand such that guide tube 240 operatively coupled thereto radially extends in an askew or generally orthogonal direction. Expandable member 210 may also be structurally or materially configured such that at least some continuous blood flow is maintained, e.g., with only minor disruption to flow, while the expandable member 210 is in its expanded position and/or during the transition to the expanded position. Expandable member 210 may be structurally or materially configured to provide additional support to the vessel at a treatment site, for example, by expanding in such a way as to contact vessel walls. In addition, expandable member 210 may be structurally or materially configured to snare an elongate member. In this regard, FIGS. 2A and 2B illustrate an embodiment having an expandable member 210 in a expanded position and FIGS. 1A and 1B illustrate an embodiment having an expandable member 210 in a collapsed position Expandable member 210 may be structurally or materially configured to be movable between a collapsed position and an outwardly extending, expanded position. In addition, expandable member may be selectively actuated between the two positions. Expandable member 210 may be slideably actuated, inflatably actuated, self-expanding, spring actuated, combinations of the same, or actuated via any other mode of actuation.

In accordance with an embodiment, a guide device is deployable through a vessel to a treatment site. The guide device deploys an endovascular tool to the treatment site and channels the tool in a direction generally normal or off axis to the longitudinal axis of a stent device. In a further embodiment, the guide device may be detectable within the body with the use of ex vivo detectors, thereby facilitating the generally accurate positioning of the guide device.

A guide device may comprise an expandable member configured to expand radially and a guide tube operatively coupled to the expandable member to channel in an endovascular tool in an askew, generally radial, or generally orthogonal direction. Askew, as used herein, describes a direction that is generally at an angle from the path of delivery. In an embodiment, the expandable member bends or extends outwardly and thus expands in response to a compression force that may be applied via the longitudinal displacement of an elongate member relative to another elongate member. In other embodiments, an inflatable member may facilitate the expansion of the expandable member. The distal end of the guide tube or other portions may comprise radiopaque material to facilitate generally accurate positioning within the body.

Method of use may comprise deploying through a vessel the guide device to a treatment site, and may further comprise outwardly extending or expanding an expandable member and channeling a subsequent tool (e.g., for puncture, cannulation, etc.) to the selected target. The guide device may be positioned with the use of a detector. An endovascular tool may be deployed through the guide device to the selected treatment site.

Other aspects of the present disclosure involve endovascular targets that are configured to anchor into a branch vessel and facilitate fenestration of an aortic graft, stent, or stent graft while maintaining continuous aortic downstream perfusion throughout the stent deployment and fenestration.

Another aspect involves a reverse cannulation system, particularly useful for stenting the abdominal aorta proximate the renal arteries and stenting the renal artery. An embodiment of the system comprises a puncturing tool entering and piercing a stent graft from the renal artery side, a snare device entering from the abdominal aorta side. The snare device captures the puncture tool and pulls the tool with its accompanying guidewire through to the abdominal aorta access point. A stent device is deployed along this guide wire to stent the renal artery.

For example, expandable member 210 may be slideably actuated to an expanded position. Such expansion may be in response to corresponding longitudinal displacement of a second elongate member 230 relative to a first elongate member 220, which applies a compression force or tension force to expandable member 210. As such, expandable member 210 at a first end may be connected to first elongate member 220, and the opposite second end is connected to second elongate member 230, such that expandable member 210 is deformed generally radially in response to selective axial displacement of second elongate member 230 relative to first elongate member 220. Collapsing expandable member 210 may be performed by selective axial displacement opposite that required to expand.

Figures 3, 4:
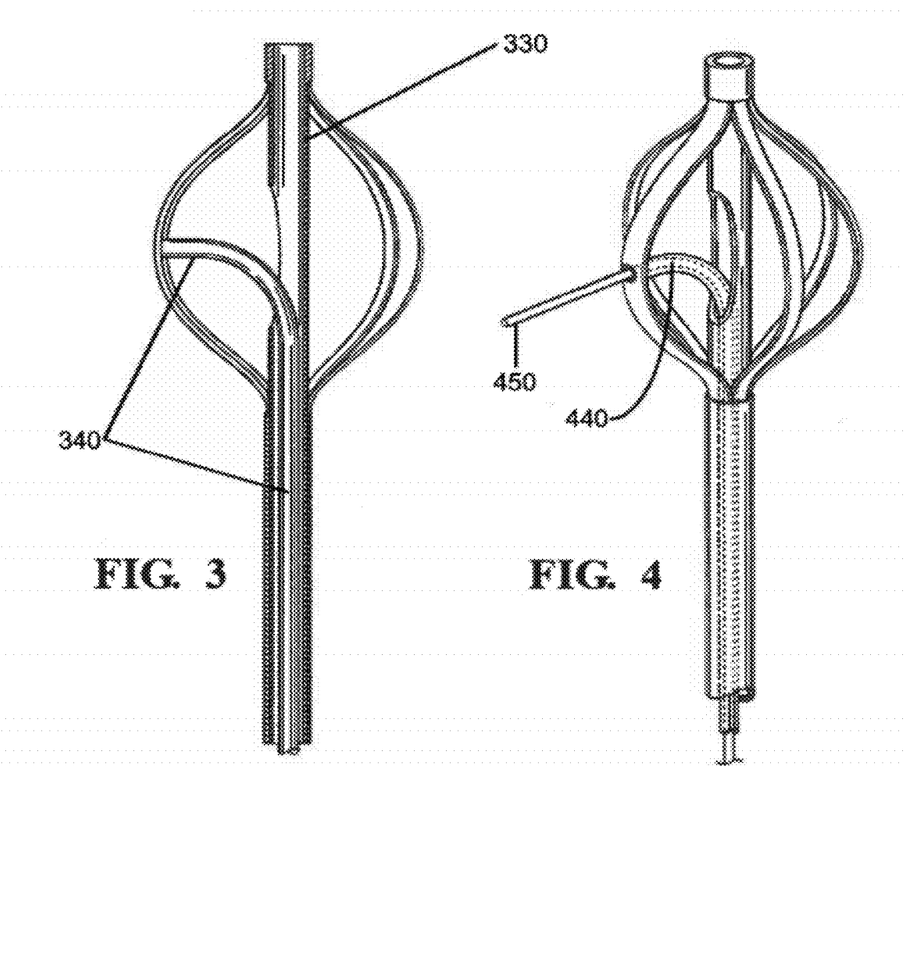
FIG. 3 illustrates a cross-section at a side view of an embodiment in an expanded position.
FIG. 4 illustrates a perspective view of an embodiment in an expanded position with a fenestration tool deployed through the distal end of a third elongate member.

In such an embodiment, first elongate member 220 may comprise a first lumen, and second elongate member 230 may comprise a second lumen and a side opening 231. Second elongate member 230 may be disposed along the first lumen, and side opening 231 may be adjacent to expandable member 210. In one embodiment, guide tube 240 may be slideably housed along the second lumen of second elongate member 230, and guide tube 240 may pass through side opening 231 to connect with expandable member 210. For example, FIG. 3 illustrates a cross-sectional view of guide tube 340 disposed along the lumen of second elongate member 330. In an alternative embodiment, a second elongate member does not comprise a side opening. In such an embodiment, the guide tube is slideably housed in the first elongate member lumen and disposed alongside the second elongate member.

As used herein, an "elongate member" has proximal and distal ends and is capable of passing through a vessel. Typically, an elongate member is flexible, especially when an elongate member is required to traverse through tortuous vasculature. Examples include a guidewire, catheter, optical fiber, or the like. An elongate member may comprise a lumen over the entire distance or a part thereof or may be solid throughout. An elongate member may comprise a blunt, rounded, or tapered distal tip, to name a few, and may be characterized by varying degrees of rigidity or softness, which may further vary along the length of the elongate member. Elongate members may have any cross-sectional shape including circular, oval, triangular, square, polygon shaped or randomly shaped. An elongate member, or any portion thereof, may be hydrophilic or hydrophobic. As used herein, a "catheter" and/or "tube" is an elongate member comprising a lumen extending through from the proximal end to the distal end.

Typical materials used to construct an elongate member can comprise materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenylene Ether (PPE), Modified Polyphenylene Ether (Mod PPE), Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylenes (PTFEs), expanded Polytetrafluoroethylenes (ePTFEs), Polyvinylidene Fluoride (PVDF), Perfluoroalkoxy (PFA). Other commonly known medical grade materials include elastomeric organosilicon polymers, polyether block amide or thermoplastic copolyether (PEBAX) and metals such as stainless steel and nickel/titanium alloys.

With reference back to FIGS. 1A, 1B, 2A, and 2B, another expansion mechanism may comprise inflatable actuation, such as via an inflatable member. For example, guide device 200 may comprise a balloon locatable within expandable member 210 that upon inflation outwardly extends expandable member 210. The inflatable member may be deflated and then confined by expandable member 210 when expandable member 210 transitions back to its collapsed position for withdrawal.

Alternatively, expandable member 210 may be made to self-expand upon release from a constraining mechanism such as a sheath. In such embodiments, expandable member 210 may be fabricated from shape-memory alloys or polymers such as stainless steel (SST), nitinol, polyurethanes, or the like such that it is configured as a passively expanding device. Guide device 200 may comprise any configuration or materials that facilitate expandable member 210 movement between its collapsed position and its outwardly extending expanded position.

In an embodiment, expandable member 210 may comprise bendable elements that are outwardly extendable. In addition, expandable member 210 may comprise a discontinuous or open structure when in the expanded position. A discontinuous or open structure permits fluid to flow across expandable member 210 with only minor fluid disruption. Maintaining downstream perfusion also relates to cannulation accuracy in the fact that guide device 200 need not withstand or resist pressures associated with temporary occlusion. For example, expandable member 210 may comprise bendable elements that separate from each other, creating space therebetween, as these elements outwardly extend, such as a malecot structure, mesh member, or a flexible tube with diagonal or longitudinal slits. Similarly, expandable member 210 may comprise at least one slat 211 connected at one end to first elongate member 220 and connected at the other end to second elongate member 230. Expandable member 210 may be integral with first elongate member 220, second elongate member 230, or a separate structure connected thereto.

The expansion of expandable member 210 may be radially symmetrical or only occur about a fraction of the perimeter of expandable member 210 creating radial asymmetry. Moreover, the distance that expandable member 210 expands or outwardly extends from the longitudinal axis may vary about the perimeter of expandable member 210 or be uniform. Such variations providing an asymmetrical profile to expandable member 210 may yield various benefits such as a wider turning radius or greater flexibility in the types of endovascular tools deployable through guide tube 240. For example, in an embodiment, expandable member 210 may comprise different materials with varying degrees of rigidity such that one side of expandable member 210 outwardly extends more so than the opposite side.

Expandable member 210 comprises a flexible material that is sufficiently rigid and strong enough to outwardly extend distal tip 241 and maintain its expanded position during a procedure. In addition, expandable member 210 may comprise a material that is sufficiently rigid to support the vessel wall during a procedure, such as a fenestration procedure. Expandable member 210 may have a generally curved profile when in an expanded position to minimize vessel wall trauma about any points of contact. Expandable member 210 may be comprised of any number of biocompatible materials including nitinol, silicon, latex, polyurethane, polyvinyl chloride, polysiloxanes, polycarbonate, polyethylene, nylon, PTFEs (e.g., ePTFEs), stainless steel, or any biocompatible material, including combinations of the foregoing.

The width or diameter of expandable member 210 in its expanded position may be adjustable across a range of widths or diameters. For example, the expandable member 210 in its expanded position may comprise a range of widths or diameters within the following values: about 1 mm to about 65 mm, about 2 mm to about 45 mm, or about 3 mm to about 30 mm. As such, guide device 200 of a certain configuration may be adaptable to a variety of vessel diameters. Similarly, guide device 200 may be scalable, and thus, utilized in a variety of applications, such as procedures in the peripheral vasculature.

Expandable member 210 may comprise a radiopaque, echogenic, or magnetic material, or any other material capable of ex vivo detection. This material may be an integral part of member 210, a coating, or a separate marker connected thereto.

In various embodiments, expandable member 210 may be configured to be a vessel diameter-measuring device. For example, guide device 200 may comprise a calibrated scale on the proximal end of second elongate member 230 so that the degree of expansion correlates to an axial position on second elongate member 230. Knowing the vessel diameter can assist with determining the appropriate diametrical size of the stent or stent graft to utilize. In addition, applying an internally distensive force while measuring the vessel diameter may further assist in selecting a stent or stent graft. The force applied by the device during measurement should correlate to the force applied by a stent or stent graft in the same place.

Guide tube 240 may be operatively coupled or connected to expandable member 210 such that when expandable member 210 moves to its expanded position, distal tip 241 radially or outwardly extends therewith. Guide tube 240 may be connected such that an endovascular tool may pass through the distal end of guide tube 240. As such, expandable member 210 may comprise an aperture 213. Aperture 213 is any opening located on expandable member 210 that permits an endovascular tool to pass through guide tube 240 with obstruction from expandable member 210. Guide tube 240 may be connected to expandable member 210 such that the distal exit of guide tube 240 is coincident the aperture 213. In other embodiments, in lieu of an aperture 213, the guide tube may be tangentially connected to expandable member 210 such that an endovascular tool may pass through guide tube 240.

In an embodiment, guide tube 240 comprises any structure configured to guide an endovascular tool to a site radial, generally orthogonal, or otherwise askew or off-axis the path of delivery 250. For example, guide tube 240 can comprise an elongate member having a proximal and distal end with a lumen therethrough Alternatively, guide tube can comprise a half tube, trough, or some other rail- or track-like configuration to guide the endovascular tool in an askew direction. In addition, guide tube 240 may direct an endovascular tool, such as that described in U.S. patent application Ser. No. 13/273,111 to Cully et al., in a substantially orthogonal direction or substantially constant angle throughout the range of expanded position diameters or widths.

Guide tube 240 may be modified to have a variety of structural properties as is suited for the endovascular tool to be delivered. For example, guiding a fluid via guide tube 240 may not require the same structural properties as would be required from a piercing catheter or the like. Similarly, guide tube 240 can have a collapsible or flimsy configuration that expands as the endovascular tool passes through its lumen, if present. This collapsible configuration can reduce the profile of guide device 200 as traverses through the vasculature to the treatment site.

Guide tube 240 operatively couples or connects to expandable member 210 such that guide tube 240 outwardly or radially extends when expandable member 210 is its expanded position. In one embodiment, distal tip 241 is movable between a first position, in which the end of distal tip 241 is generally coaxial or generally parallel with expandable member 210 in its collapsed position, and a second position, in which distal tip 241 extends askew or in a generally orthogonal or radial direction, as expandable member 210 is expanded. Distal tip 241 of guide tube 240 may be operatively coupled to expandable member 210 coincident aperture 213. In a different embodiment, distal tip 241 of the guide tube 240 may be coupled tangentially to expandable member 210. However, the present disclosure includes any configuration that radially extends guide tube 240 when expandable member 210 is its expanded position such that an endovascular tool can pass through guide tube 240.

In an exemplary embodiment, the distal tip 241 of guide tube 240 or a portion thereof comprises a radiopaque, echogenic, or magnetic material, or any other material capable of ex vivo detection. This material may be an integral part of tip 241, a coating, or a separate marker connected thereto.

In various embodiments, guide device 200 may be configured to be a drug delivery device. For example, a drug may reside within expandable member 210 such that the drug is generally confined while expandable member 210 is in a collapsed position. Once expandable member 210 reaches the treatment site, expandable member 210 may expand to release the drug into the vasculature. In other embodiments, the drug may be injected into guide tube 240, or an endovascular tool may comprise a drug delivery tool that can be delivered through guide tube 240 toward a desired treatment site. Such tools may be configured to penetrate a mass and deliver a drug directly into the mass.

In an embodiment, a method for using guide device 200 such as described herein may comprise the steps of deploying guide device 200 into a vessel and outwardly extending the expandable member 210 to an expanded position and thereby causing movement of distal tip 241 to its second position. Such expansion may be executed without substantially disrupting fluid flow through the vessel. Distal tip 241 in the second position may extend toward a treatment site on the vessel wall, thereby directing an endovascular tool passed through guide tube 240 toward the treatment site.

In an embodiment, expandable member 210 is outwardly extended by applying a compression force to expandable member 210, such as through longitudinal displacement of second elongate member 230 relative to first elongate member 220, thereby radially or outwardly extending distal tip 241. Alternatively, expandable member 210 is outwardly extended by inflating an inflatable member.

A further embodiment comprises selectively positioning guide device 200 with the assistance of a detector, ex vivo, showing an in vivo position of the distal tip 241 or expandable member 210. Then, an endovascular tool, such as that described in U.S. patent application Ser. No. 13/273,111 to Cully et al., may be advanced through the distal end of guide tube 240. For example, FIG. 4 illustrates an endovascular tool 450 advanced through guide tube 440. A further embodiment involves puncturing a selected site with endovascular tool 450. A further embodiment involves injecting a contrast agent into guide tube 440 or an endovascular tool to verify a side branch has been fenestrated and/or cannulated or verify that the side branch is in fluid communication with the main vessel.

Figure 5A:
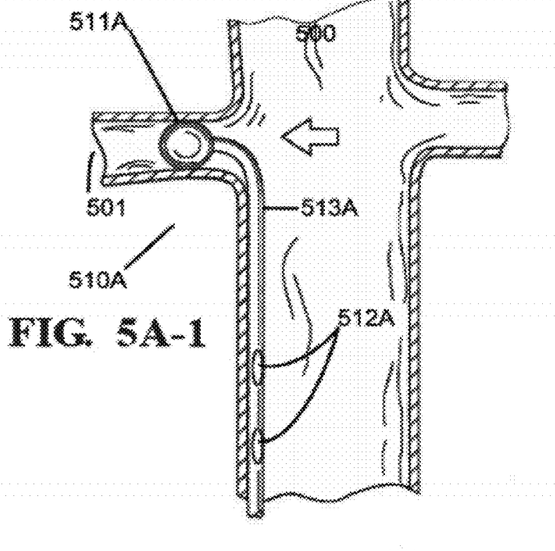
FIG. 5A illustrates a cross-section view of an embodiment of an endovascular target with a inflatable distal anchor positioned in a branch vessel and a side view of the endovascular target.
FIG. 5B illustrates a cross-section view of an embodiment of an endovascular target with a helical distal anchor positioned in a branch vessel and a side view of the endovascular target.
Figure 5A:
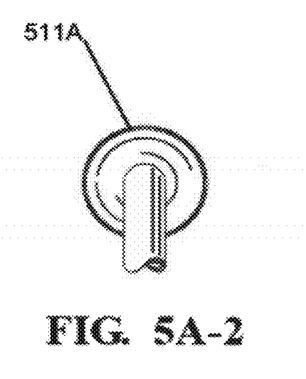
Figure 5B:
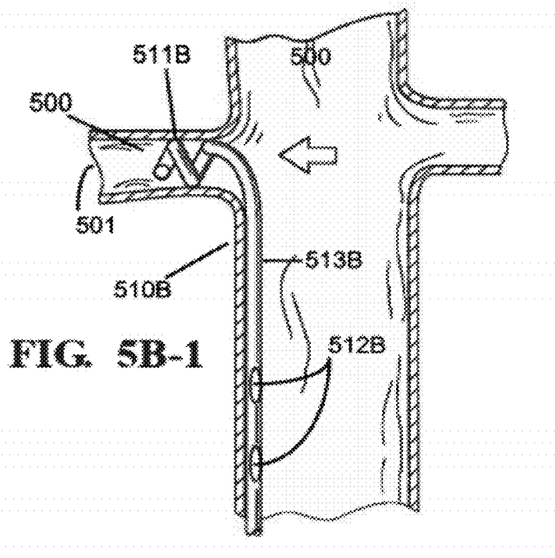
Figure 5B:
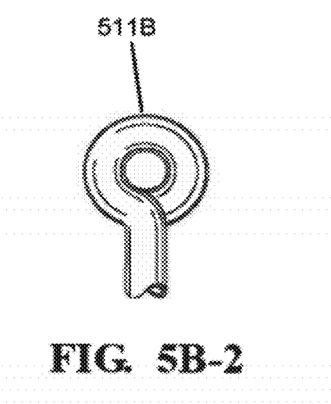

With reference to FIGS. 5A and 5B, various embodiments of the present disclosure comprise an endovascular target 510A,B. Endovascular target 510A,B is a temporary or permanent implant that serves as a target for an endovascular tool. Endovascular target 510A,B facilitates the perfusion of fluid through a branch vessel 501. An embodiment of endovascular target 510A,B comprises an elongate member 513A,B, with a lumen at least in the distal region of elongate member 513A,B and at least one opening 512A,B in the wall of elongate member 513A,B accessing the lumen, and a distal anchor 511A,B.

In an exemplary embodiment, distal anchor 511A,B is configured to be positioned fixedly in branch vessel 501. Distal anchor 511A,B may be integral with elongate member 513A,B or a separate structure attached thereto. Distal anchor 511A,B may comprise a helix (e.g., as illustrated in FIG. 5B), a ring, a perforated disc, an inflatable member (e.g., as illustrated in FIG. 5A) or any structure configured to position fixedly in branch vessel 501. Distal anchor 511A,B may comprise detectable material such as a magnetic, radiopaque, echogenic, or fluorescent material, or any other material capable of ex vivo detection, such as with the use of electromagnetic radiation, fluoroscopy, an angioscope, or otherwise. In the case of the inflatable member, the inflation medium may be radiopaque. In exemplary embodiments, the diameter of distal anchor 511A,B across the widest portion thereof when it is fixedly positioned is from about 1 mm to about 15 mm, from about 4 mm to about 7 mm, or from about 3 mm to about 6 mm. Distal anchor 511A,B may be comprised of any number of materials including silicon, latex, polycarbonate, polysiloxane, polyurethane, polyvinyl chloride, polyethylene, nylon, PTFEs (e.g., ePTFEs), nitinol, or any biocompatible material, including combinations of the foregoing. In another embodiment, distal anchor 511A,B comprises a coating of heparin or other anti-coagulant agent.

In embodiments, there may be any number, position, or configuration of opening 512A,B in the wall of elongate member 513A,B. Opening 512A,B facilitates perfusion of the side branch vasculature. In an exemplary embodiment, the position of opening 512A,B along elongate member 513A,B is such that opening 512A,B is located in main vessel 500 beyond the reach of a stent deployed in main vessel 500 when distal anchor 511A,B is fixedly positioned in branch vessel 501. This will allow a fluid such as blood to enter the lumen and facilitate perfusion of the side branch vasculature and downstream organs (e.g., kidneys). Opening 512A,B may be configured such that blood readily passes through opening 512A,B and into the lumen of elongate member 513A,B, in a retrograde direction from that of the main vessel if required. A flap may be utilized to facilitate one-way flow through opening 512A,B.

In other embodiments, the wall of elongate member 513A,B is not compromised. Stated another way, there is no opening for perfusion. The lumen extends to the hub of elongate member 513A,B where the clinician may utilize it for perfusion of the side branch and its associated vasculature by injecting fluid, such as autologous blood or otherwise, with a syringe. In this embodiment, a clinician may see fit to modify by creating opening 512A,B for retrograde perfusion by skiving the side of elongate member 513A,B, for example, with a scalpel blade.

Another embodiment comprises the steps of deploying endovascular target 510A,B as described herein into branch vessel 501 via main vessel 500 and fixedly positioning distal anchor 511A,B in branch vessel 501.

In an embodiment, a guide system may comprise an endovascular target and a guide device as described herein to facilitate the lateral and rotational positioning of the guide device. A further embodiment comprises a detector, an angioscope, or the like to facilitate the lateral and rotational positioning of guide device.

Another embodiment comprises the steps of deploying an endovascular target to a treatment area and positioning the endovascular target into branch vessel 501. Further steps involve deploying a primary stent device in main vessel 500, deploying a guide device as described herein to the grafted area, expanding the expandable member, and positioning the guide device relative to the endovascular target 510A,B with the use of a detector, an angioscope, or the like. A further embodiment comprises deploying an endovascular tool through the guide tube to pierce the stent device proximate distal anchor 511A,B. Other embodiments may comprise deploying a balloon device to the puncture site to expand the perforation and deploying a branch stent device to stent branch vessel 501. Embodiments of the branch stent device may comprise a stent device, as that term is defined herein, gaskets, seals, flanges, self-expanding configurations, balloon-expanding configurations, or any combination of the foregoing.

Another embodiment comprises a guide device as described herein, configured to permit an angioscope to pass through the guide tube, a stent device comprising a transparent to translucent stent wall, and an angioscope. Once the stent device is deployed, the angioscope advances through the guide tube of the guide device. The guide device facilitates the lateral and rotational positioning. The angioscope permits the visual verification a branch vessel ostium through the transparent to translucent stent graft wall so that a fenestration tool or piercing guide tube may be deployed through the guide tube to fenestrate the stent graft at the branch vessel junction. A further embodiment may comprise deploying a balloon device to the pierced stent to expand the perforation and deploying a branch stenting device to stent the branch vessel.

Figures 6A, 6A:
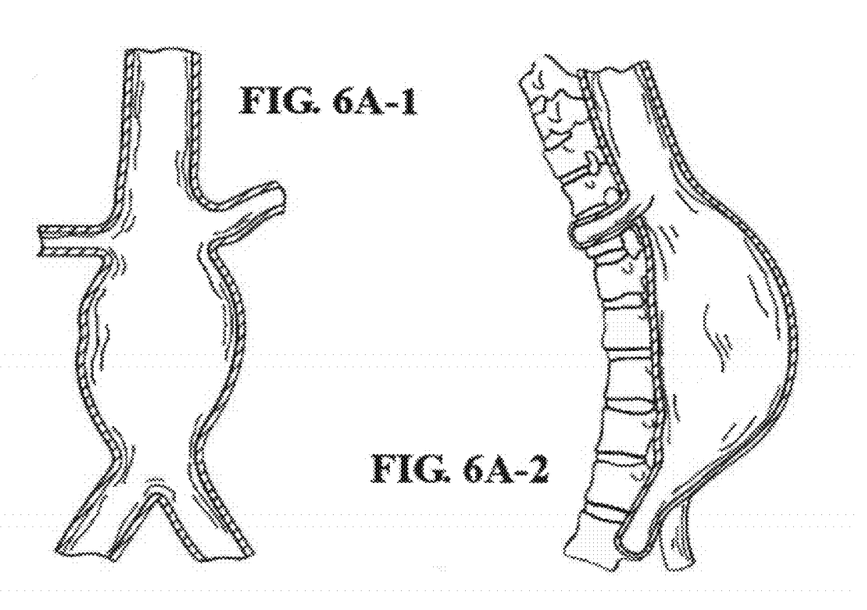
FIGS. 6A-6M illustrate steps of an embodiment to stent a main vessel and a branch vessel.
Figures 6B, 6B:
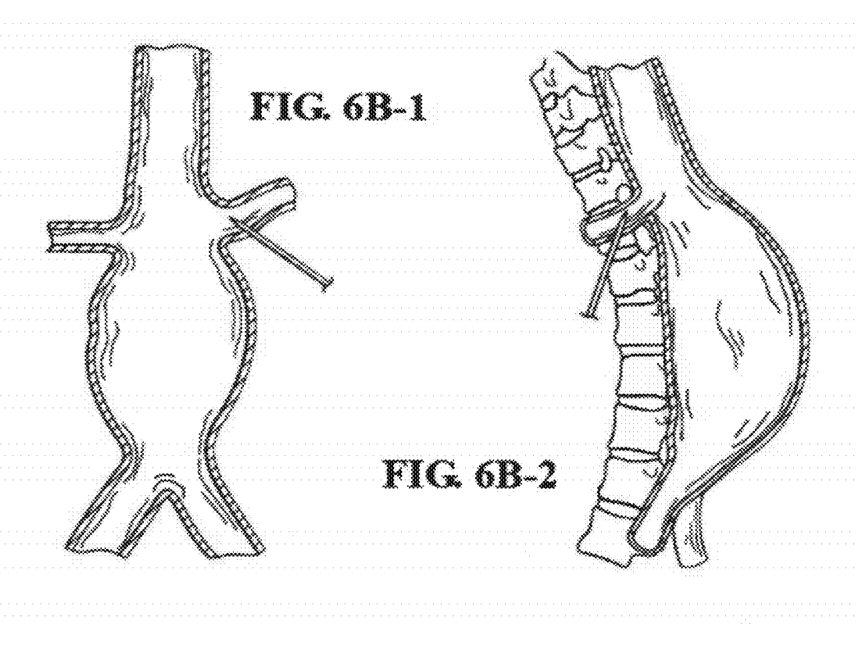
Figures 6C, 6C:
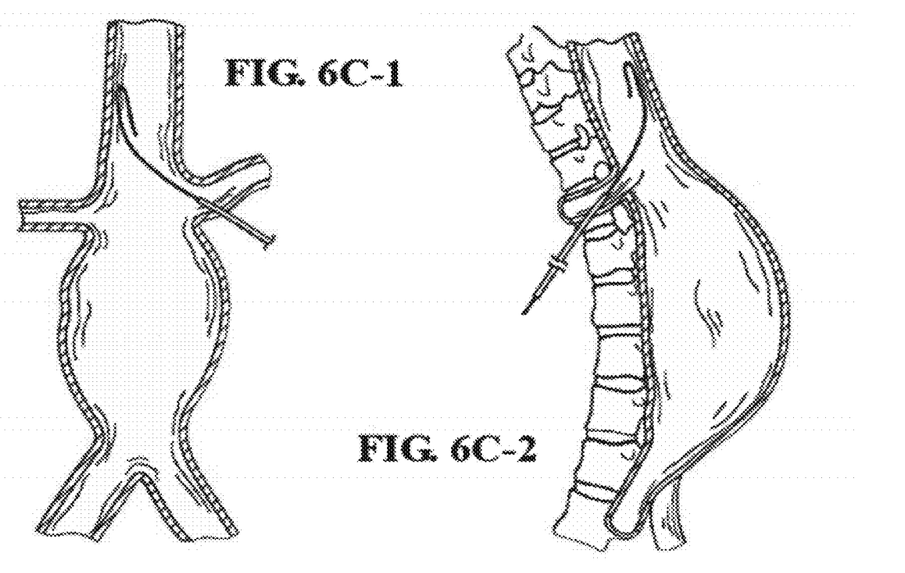
Figures 6D, 6D:
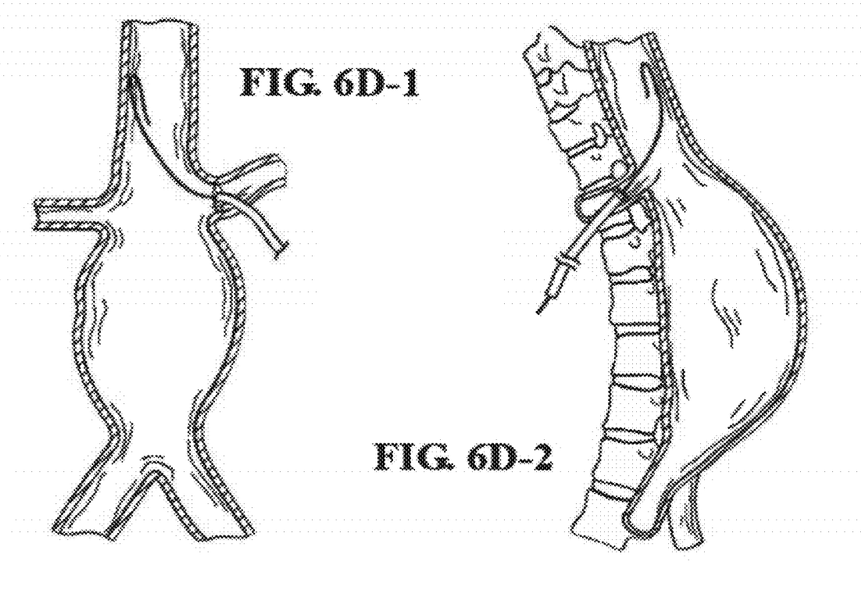
Figures 6E, 6E:
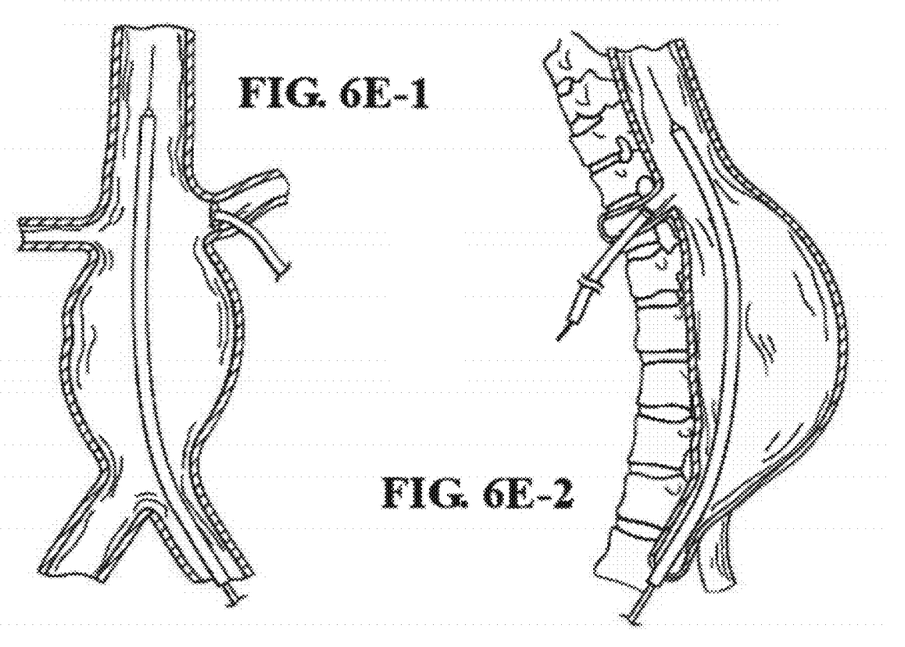
Figures 6F, 6F:
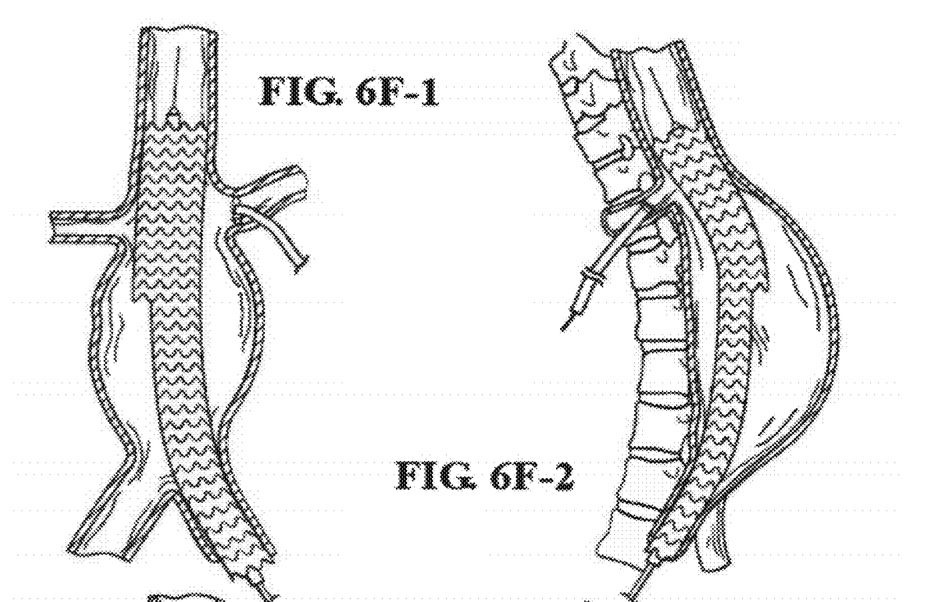
Figures 6G, 6G:
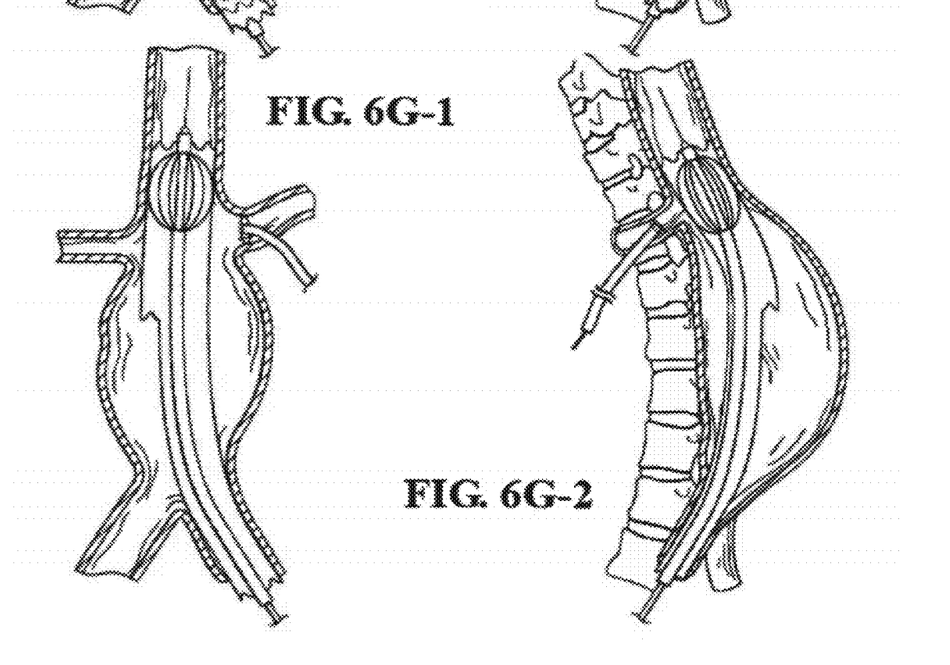
Figures 6H, 6H:
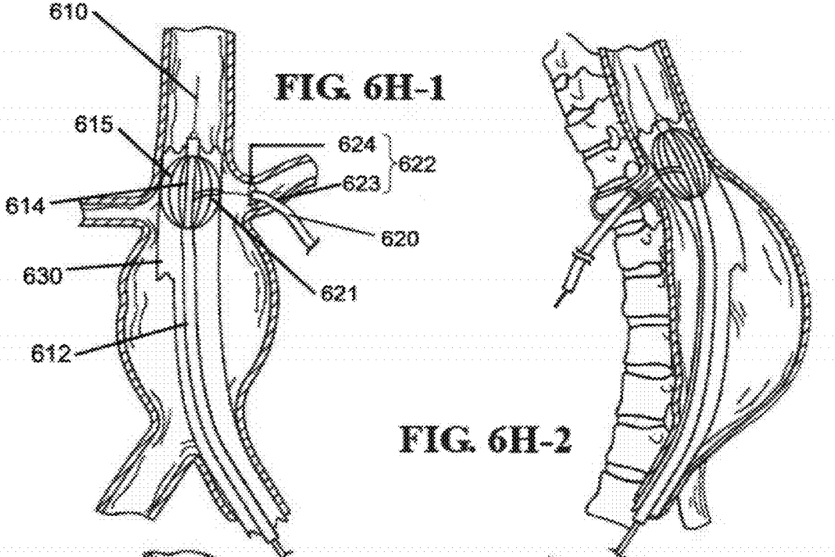
Figures 6I, 6I:
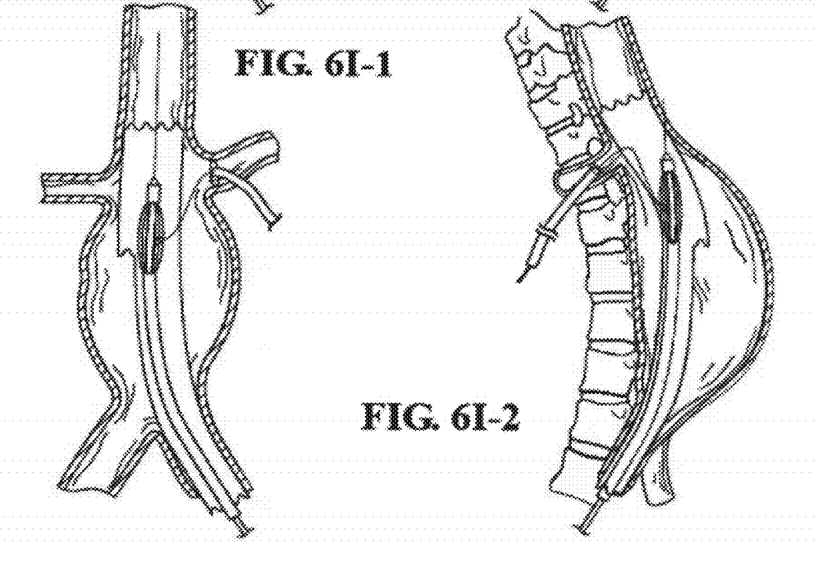
Figures 6J, 6J:
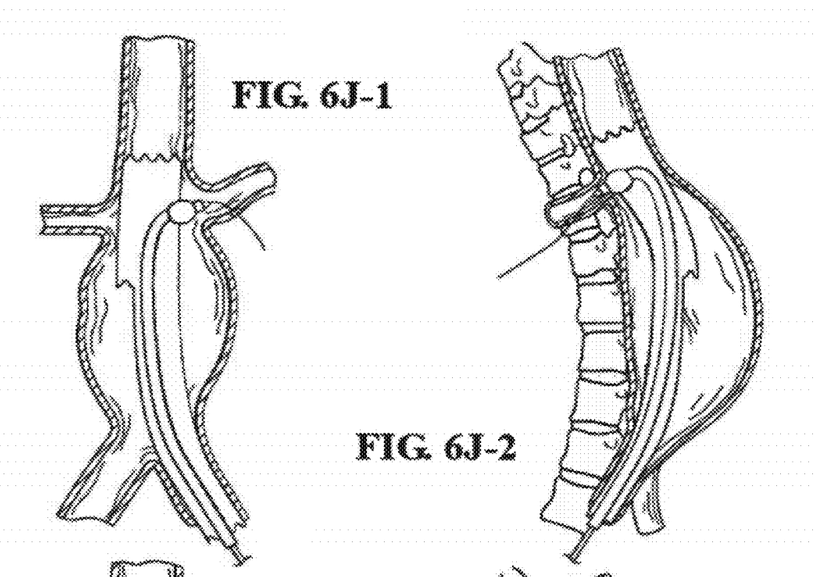
Figures 6K, 6K:
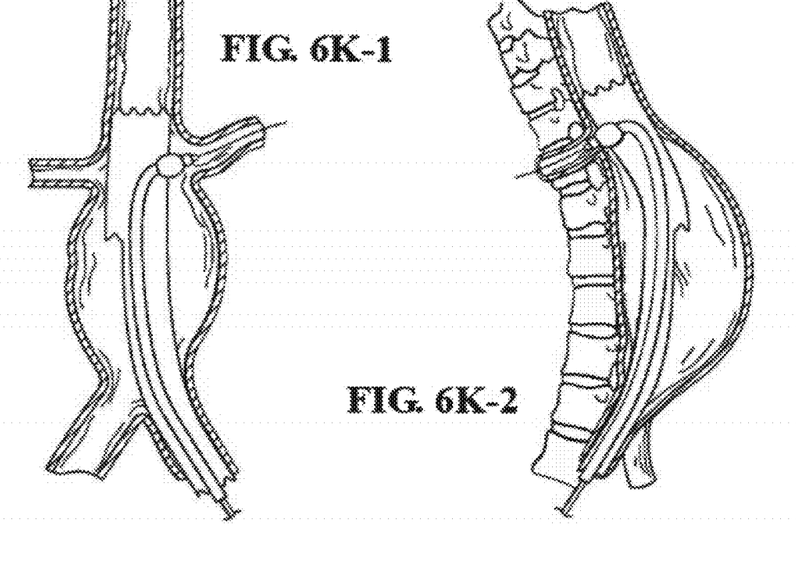
Figures 6L, 6L:
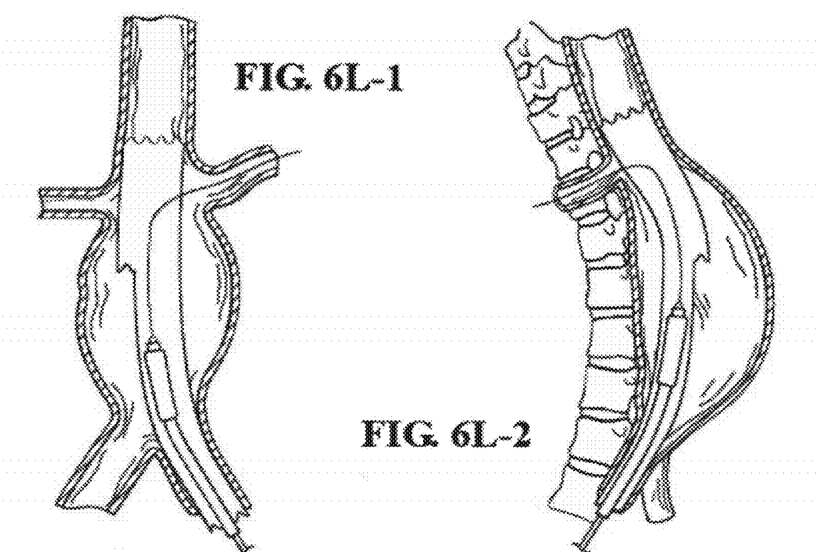
Figures 6M, 6M:
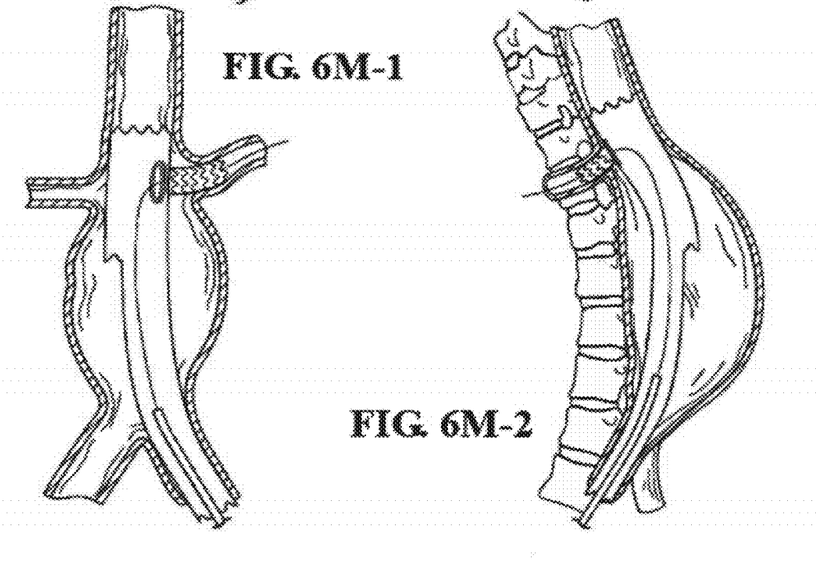

In accordance with another exemplary embodiment and with reference to FIG. 6H, a reverse cannulation system comprises a snare device 610 comprising an expandable member 615 as described herein, puncture guide device 620, and a primary stent device 630. The primary stent device 630 comprises a stent or a stent graft, both of which may be balloon expanding or self-expanding. An embodiment of a stent device comprises graft materials or fibers configured to prevent ripping or tearing upon puncturing or ballooning. In some embodiments, expandable member 615 may expand the primary stent device 630. Once the stent is in position, the stent wall is fenestrated coincident the branch vessel from the exterior of the stent toward the interior with a puncture tool 621. A puncture guide catheter 622 supports and guides a puncture tool 621 to the piercing site on the stent graft.

Puncture guide device 620 comprises a puncture guide catheter 622 having at least one lumen 623 with a perfusable anchor 624 at distal exterior of catheter 622 and a puncture tool 621 supportable by the puncture guide catheter 622. In an exemplary embodiment, the puncture guide catheter 622 provides the required column strength via lumen 623 to the puncture tool 621 for piercing the primary stent device 630. Puncture guide catheter may comprise a second lumen to allow for perfusion of blood to the kidney. Blood may be injected into second lumen as needed. The second lumen may be coated with heparin.

In accordance with an exemplary embodiment, puncture tool 621 comprises an elongate member and a tapered or sharp tip at a distal end. In other embodiments, puncture tool 621 may comprise a piercing catheter. In other embodiments, puncture tool 621 is energized with electromagnetic radiation, such as radio-frequency energy and the like, or mechanical energy.

An embodiment of perfusable anchor 624 can comprise at least one inflatable member connected to the distal exterior of catheter 622. The inflatable member is of sufficient size to stabilize catheter 622 in the branch vessel. Other embodiments of perfusable anchor 624 comprise at least one ring connected to the distal exterior of catheter 622, such that fluid passes through the ring and the ring assists in anchoring punch guide catheter 622. Perfusable anchor 624 may comprise any number or variety of ringed geometric shapes connected to the distal exterior of catheter 622. Perfusable anchor 624 may comprise an expandable, perfusable mechanical anchor, such as an expandable braid, in lieu of an inflatable member. Other embodiments of perfusable anchor 624 may comprise a perforated disc or the endovascular target as described herein.

In accordance with an embodiment, snare device 610 comprises an expandable member 615 as described herein. In an embodiment, first elongate member 612 and second elongate member 614 connect to an end opposite the other of expandable member 615 such that the longitudinal displacement of second elongate member 614 relative to first elongate member 612 expands and collapses expandable member 615. Other embodiments of snare device 610 comprise the guide device as described herein. Use of expandable member 615 also allows for propping or bolstering the stent graft inner diameter in preparation for an in-situ fenestration. This added support may be helpful when puncturing strong stent graft material. Embodiments of snare device 610 may be configured to capture, hook, entangle, or the like a guidewire or puncture tool.

With reference to FIGS. 6A-6M for purposes of illustration, another embodiment comprises the steps of accessing a side-branch through a lumbar access with a needle and/or lumbar stick (FIG. 6A-6B); advancing a guide wire through the needle and gaining access through the branch vessel (e.g., renal artery) to the main vessel (e.g., aorta) (FIG. 6C); removing the needle and/or lumbar stick; advancing a puncture guide device over the guide wire (FIG. 6D); positioning the puncture guide device as described herein in the branch vessel near a junction with a main vessel (FIG. 6D); withdrawing the guide wire from the main vessel (FIG. 6E); advancing a primary stent device through the main vessel proximate the junction (FIG. 6E); deploying the primary stent device (FIG. 6F); advancing a snare device as described herein so that the expandable member is proximate the junction (FIG. 6G); expanding the expandable member (FIG. 6G); advancing a puncture tool through the puncture guide catheter to pierce the primary stent device and into the expandable member (FIG. 6H); collapsing the expandable member and withdrawing the expandable member with the puncture tool in tow (FIG. 6I). Because of these steps, an elongate member is threaded from a secondary access point into a branch vessel to the main vessel and out through a primary access point.

A further embodiment comprises the step of advancing a balloon catheter into the puncture site (FIG. 6J); ballooning the punctured site to further open the puncture (FIG. 6J); withdrawing the elongate member from the secondary access point into the branch vessel (FIG. 6K); withdrawing the balloon catheter; advancing the secondary stent device through the punctured site (FIG. 6L); and deploying the branch stent device (FIG. 6M). Embodiments of the branch stent device may comprise gaskets, seals, flanges, self-expanding configurations, balloon-expanding configurations, or any combination of the foregoing.

Numerous characteristics and advantages have been set forth in the preceding description, including various alternatives together with details of the structure and function of the devices and/or methods. The disclosure is intended as illustrative only and as such is not intended to be exhaustive. For example, while the disclosure has been described primarily with reference to aortic applications, illustrative embodiments may be used in connection with other vessels having branched vessels extending therefrom. It will be evident to those skilled in the art that various modifications may be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed:

1. A guide device deployable through a vessel comprising:
   an expandable member movable between a collapsed position and an outwardly extending, expanded position; and
   a guide tube operatively coupled to the expandable member and having a distal tip which is moveable between a first position generally parallel with the expandable member in the collapsed position and a second position askew to the first position,
   a first elongate member comprising a first lumen; and
   a second elongate member comprising a second lumen and a side opening,
   wherein the guide tube is disposed along the second lumen and the second elongate member is disposed along the first lumen,
   wherein the expandable member extends between a first end connected to the first elongate member and an opposite second end connected to the second elongate member, such that the expandable member is radially displaceable in response to longitudinal displacement of the second elongate member relative to the first elongate member, and
   wherein the guide tube actuates between the first and second positions in response to contraction and expansion of the expandable member between the collapsed and expanded positions, respectively.

2. The guide device of claim 1, wherein the second position is generally orthogonal to the first position.

3. The guide device of claim 1, wherein the expandable member comprises an aperture and the distal tip of the guide tube is connected to the expandable member coincident the aperture.

4. The guide device of claim 1, wherein the distal tip is movable between the first position to the second position as the expandable member expands in response to corresponding longitudinal displacement of the second elongate member relative to the first elongate member.

5. The guide device of claim 1, wherein the expandable member has a discontinuous structure to allow perfusion of fluid therethrough when in an expanded position.

6. The guide device of claim 5, wherein the expandable member has a discontinuous structure to allow perfusion of fluid therethrough when moving between the expanded and collapsed positions.

7. The guide device of claim 5, wherein the expandable member expands in a substantially radially symmetrical manner.

8. The guide device of claim 5, wherein the expandable member comprises at least one of a malecot structure, a mesh member, a tube with diagonal or longitudinal slits, and at least one slat.

9. The guide device of claim 1, wherein the expandable member comprises nitinol.

10. The guide device of claim 1, wherein the distal tip of the guide tube directs endovascular tools in a direction generally orthogonal to a path of delivery.

11. The guide device of claim 1, wherein the expandable member is adjustable across a range of expanded position diameters.

12. The guide device of claim 11, wherein the distal tip of the guide tube directs devices in a direction substantially perpendicular to a path of delivery throughout the range of expanded position diameters.

13. The guide device of claim 1, wherein the distal tip comprises a radiopaque material.

14. A method for guiding an endovascular tool in a vessel comprising:
   deploying a guide device of claim 1 into a main vessel,
   outwardly extending the expandable member and thereby causing movement of the guide tube to the second position with only minor disruption of fluid flow through the vessel.

15. The method of claim 14, wherein the distal tip of the guide tube, in the second position, extends toward a treatment site on the main vessel wall, thereby directing an endovascular tool passed through the guide tube toward the treatment site.

16. The method of claim 14, wherein the expandable member is outwardly extended by applying a compression force to the expandable member.

17. The method of claim 14, further comprises selectively positioning the guide device with the assistance of a detector, ex vivo, showing an in vivo position of a radiopaque distal tip.

18. The method of claim 14, further comprises advancing an endovascular tool through a distal end of the guide tube.

19. The method of claim 18, further comprises puncturing a selected site with the endovascular tool.

20. The method of claim 19, further comprises injecting a contrast agent to verify a side branch is in fluid communication with the main vessel.

21. The method of claim 18, wherein the endovascular tool is an elongate member comprising a tapered or sharp distal end extendable through the guide tube.

* * * * *